United States Patent
Huang (10) Patent No.: US 8,691,980 B2
(45) Date of Patent: Apr. 8, 2014

(54) SALICYLIC ACID DERIVATIVES WITH FLUOROPHORES AND METHOD OF MAKING AND USING THE SAME

(75) Inventor: Sheng-Tung Huang, Taipei (TW)

(73) Assignee: National Taipei University of Technology, Taipei (TW)

( * ) Notice: Subject to any disclaimer, the term of this patent is extended or adjusted under 35 U.S.C. 154(b) by 262 days.

(21) Appl. No.: 13/075,237

(22) Filed: Mar. 30, 2011

(65) Prior Publication Data

US 2012/0252047 A1   Oct. 4, 2012

(51) Int. Cl.
*C07D 417/04* (2006.01)
*C07D 413/04* (2006.01)
*C07D 265/38* (2006.01)
*C07D 211/06* (2006.01)

(52) U.S. Cl.
CPC ............ *C07D 265/38* (2013.01); *C07D 211/06* (2013.01); *C07D 417/04* (2013.01); *C07D 413/04* (2013.01)
USPC ............ 544/101; 546/101; 548/159; 548/217

(58) Field of Classification Search
None
See application file for complete search history.

(56) References Cited

PUBLICATIONS

Grant & Hackh's Chemical Dictionary (5th Ed. 1987) at p. 148.*
Huang et al., Design and Synthesis of a Long-Wavelength Latent Fluorogenic Substrate for Salicylate Hydroxylase: A Useful Fluorimetric Indicator for Analyte Determination by Dehydrogenase-Coupled Biosensors. Analytical Chemistry, 2010, 82, 7329-7334.*
Huang et al: Synthesis of a New Long-Wavelength Latent Fluorimetric Indicator for Analytes Determination in the DT-Diaphorase Coupling Dehydrogenase Assay System; Biosensors and Bioelectronics 23 (2008) 1793-1798.
Kang et al: A New Class of Macrocyclic Receptors From IOTA-Peptides; J. Am. Chem. Soc. 2007, 129, 1486-1487.
Huang et al: Development of a Long-Wavelength Fluorescent Probe Based on Quinone-Methide-Type Reaction to Detect Physiologically Significant Thiols; Analytica Chimica Acta 620 (2008) 120-126.
Cham et al.: Simultaneous Liquid-Chromatographic Quantitation of Salicylic Acid, Salicyluric Acid, and Gentisic Acid in Plasma; Clinical Chemistry, vol. 25, No. 8, 1979.
Trinder et al.: Rapid Determination of Salicylate in Biological Fluids; Biochemistry Department, Royal Infirmary, Sunderland, Co. Durham, Nov. 14, 1953.

* cited by examiner

*Primary Examiner* — Michael Barker
*Assistant Examiner* — Po-Chih Chen
(74) *Attorney, Agent, or Firm* — Schmeiser, Olsen & Watts, LLP (57) ABSTRACT

A latent fluorophore is derived from salicylic acid, and containing a fluorogenic group and a moiety represented by formula I

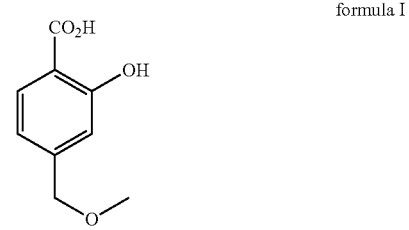

formula I wherein the fluorogenic group is directly linked to the moiety of formula I or indirectly linked thereto via a linkage structure. In addition, a method of preparing a latent fluorophore, a method of using the same and a kit containing the same are also introduced.

12 Claims, 3 Drawing Sheets

SALICYLIC ACID DERIVATIVES WITH FLUOROPHORES AND METHOD OF MAKING AND USING THE SAME

FIELD OF TECHNOLOGY

The present invention is related to a compound which can emit fluorescence through a biochemical reaction, especially a compound containing both a moiety derived from salicylic acid and a fluorogenic group in its chemical structure.

BACKGROUND

Salicylate hydroxylase (SHL) is a flavoprotein, which can catalyze conversion of salicylic acid to catechol in the presence of NAD(P)H in an aerobic environment.

An electrochemical biosensor formed by fixing both SHL and NAD(P)$^+$-dependent dehydrogenase on a Clark electrode has been reported. Said biosensor can be used in detection of various biochemical molecules by using various enzymes.

However, the electrochemical biosensor has encountered some difficulties in practical manufacture and moreover, keeping the manufactured electrode in a good condition for a long time is not easy; therefore, a resolution to solve the above problems is desired.

SUMMARY

In view of the disadvantages of the conventional technology, the present inventor has endeavored in researching a new type biosensor, and finally found a latent fluorophore (or pro-fluorophore) which can be used in biochemical analyses based on measurement of fluorescence intensity, a method of preparing the latent fluorophore, a method of biochemical analysis by using the same, and a kit for biochemical analysis containing the same.

One object of the present invention is providing a latent fluorophore derived from salicylic acid, which comprises a fluorogenic group and a moiety represented by formula I formula I wherein the fluorogenic group is directly linked to the moiety of formula I or indirectly linked thereto via a linkage structure.

In preferred embodiments, the latent fluorophore can be prepared by using various chemical synthetic methods to link a fluorogenic group to a moiety of formula I directly or indirectly via a linkage structure. The preferred examples of the latent fluorophore are as follows:

formula II formula III and formula IV wherein $R_1$ is selected from H or a $C_1$-$C_6$ alkyl.

In addition, the fluorogenic group which can be used in the present invention is preferably selected from a group consisting of the followings:

(wherein
$R_2$ is selected from H or CN,
$R_3$ is selected from (wherein each $R_4$ is independently selected from a $C_1$-$C_6$ alkyl group, benzyl, CN or a halogen atom).

Another object of the present invention is providing a method of preparing a latent fluorophore, comprising:
providing a protected salicylic acid derivative;
linking a molecule containing a fluorogenic group to the protected salicylic acid derivative; and
removing the protecting group of the salicylic acid moiety to obtain the latent fluorophore.

In an embodiment of the present invention, the protected salicylic acid derivative has a structure represented by formula V:

formula V wherein L is a leaving group.

A further object of the present invention is providing a method of biochemical analysis for determination of the amount of salicylic acid, comprising; providing a reagent comprising
salicylate hydorxylase (SHL),
a latent fluorophore which can be catalyzed by SHL, and NADH or NADPH;
adding a specimen under test to the reagent in an aerobic environment; and
measuring the fluorescence of the reagent, thereby determining the amount of salicylic acid present in the reagent.

In addition, the present invention also provides a method of biochemical analysis based on change in fluorescence intensity under catalysis of a series of enzymes, comprising:
providing a reagent comprising
salicylate hydorxylase (SHL),
a latent fluorophore which can be catalyzed by SHL,
$NAD(P)^+$, and
a $NAD(P)^+$-dependent dehydrogenase;
adding a specimen under test to the reagent in an aerobic environment; and
measuring the fluorescence of the reagent, thereby determining the amount of a biochemical molecule present in the reagent.

In an embodiment of the present invention, the $NAD(P)^+$-dependent dehydrogenase is selected from 3-hydroxybutyrate dehydrogenase, chloesterol dehydrogenase, glucose dehydrogenase or glucose-6-phosphate dehydrogenase.

Further another object of the present invention is providing a kit for biochemical analysis, which comprises:
salicylate hydorxylase (SHL),
$NAD(P)^+$,
a $NAD(P)^+$-dependent dehydrogenase, and
a latent fluorophore.

In addition, the kit can optionally contains a third enzyme for catalyzing formation of the substrate for the $NAD(P)^+$-dependent dehydrogenase.

DETAILED DESCRIPTION

In order to full describe the objects, features and effects of the present invention such that the person having ordinary knowledge in this art can understand the technical content of the present invention and put it into practice, the present invention will be described in details with reference to the following embodiments and the attached drawings.

In one embodiment of the present invention, a compound derived from salicylic acid is provided. The compound has a fluorogenic group and a moiety represented by formula I in its structure formula I In the above structure, the fluorogenic group can be directly linked to the moiety of formula I, as shown in the following formula II As an example, the structure represented by formula II wherein the skeleton of the fluorogenic group is a coumarin-like structure, can be chemically synthesized according to the following scheme:

In this scheme, compound A is a protected salicylic acid derivative, which can be prepared according to the method as stated in "Kang, S. W.; Gothard, C. M.; Maitra, S.; Wahab, A.; Nowick, J. S. *J. Am. Chem. Soc.,* 2007, 129, 1486-1487," the entire content of which is incorporated herein by reference. Of course, it is possible to prepare protected salicylic acid derivatives different from Compound A by using a protection method known to the persons having ordinary knowledge in this art without undue experiments. In addition, Br in the structure of Compound A functions as a leaving group in a substitution reaction. Other leaving groups, for example, halogen atoms other than Br, OTs and OMs, can also be used but not limited thereto.

In this scheme, Compound B is a coumarin derivative which can emit fluorescence. Compound B can be prepared according to the method as stated in "Huang, S. T.; Ting, K. N.; Wang, K. L *Anal. Chimica Acta,* 2008, 620, 120-126," the entire content of which is incorporated herein by reference. Of course, the anaglogues of Compound C can be prepared by a person having ordinary knowledge in this art without undue experiments, through reacting Compound A with other coumarin derivatives similar to Compound B. In Compound B, for example, CN can be replaced with H;

can be replaced with but not limited thereto. These Compound B analogues can be prepared according to the method as stated in "Wolfbeis, O. S.; Koller, E.; Hochmuth, P. *Bull. Chem. Soc. Jp.* 1985, 58, 731;" the entire content of which is incorporated herein by reference.

The process as shown in the above scheme is performed in two steps. In the first step, the hydroxy group of compound B is benzylation by compound A under an alkaline condition to form a benzyl ether (not shown in the scheme). In this case, $Na_2CO_3$ is used as alkali to neutralize the produced acid; however, other alkalis that do not adversely affect the benzylation reaction, such as KOH, can be also used. In the second step, the protecting group is removed from the benzyl ether produced in the first step. Trifluoracetic acid (TFA) is used to catalyze the deprotection reaction, but other strong acids can be also used.

By the above process, compound B which can emit fluorescence is converted into compound C which does not emit fluorescene, i.e. a latent fluorophore. Compound C can be converted back into a fluorescent compound under catalysis of an enzyme; therefore, it can be used in biochemical detection.

Furthermore, the fluorogenic group can be indirectly linked to the moiety of formula I via a linkage structure to form a latent fluorophore as shown below:

(wherein $R_1$ is selected from H or $C_1$-$C_6$ alkyl); or formula IV

To synthesize the latent fluorophore of formula III, a protected salycylic acid derivative is reacted with a fluorophore in the presence of phosgene. As an example, the latent fluorophore of formula III wherein the skeleton of the fluorogenic group is a coumarin-like structure, can be prepared by a two-step process (first forming a benzyl ether, then performing deprotection) as follows:

wherein $R_2$ is selected from H or CN, and
$R_3$ is selected from:

The latent fluorophore of formula IV can be synthesized according to the method disclosed in "Huang, S. T.; Peng, Y. X.; Wang, K. L. *Biosensor & Bioelectronic* 2008, 23, 1793-1798," the entire content of which is incorporated herein by reference.

In the present invention, there is no special limitation to the fluorogenic group in the latent fluorophore molecule. For example, in some embodiments, the fluorogenic group is coumarin or its derivative; in other embodiments, the fluorogenic group is the one unlike coumarin or its derivatives.

In preferred embodiments, the fluorogeic group is selected from a group consisting of:

(wherein
$R_2$ is selected from H or CN,
$R_3$ is selected from (wherein each $R_4$ is independently selected from a $C_1$-$C_6$ alkyl group, a benzyl group, CN or a halogen atom).

In preferred embodiments, the fluorogenic group can emit fluorescence with a wavelength above 500 nm under catalysis of SHL. Owing that lots of biochemical molecules themselves can also emit fluorescence lights and these fluorescence lights are usually in a blue light region with a wavelength below 500 nm, a fluorogenic group which emits fluorescence with a wavelength above 500 nm is preferably used in a biochemical analysis to avoid interference of the biochemical molecules not under test. In a preferred embodiment, the fluorescence emitted by the fluorogenic group in the latent fluorophore has a peak emission wavelength of about 550~650 nm.

Furthermore, in the process of synthesis of the latent fluorophore, the salicylic acid derivative may be reacted with the fluorogenic group in an equivalent ratio other than 1:1. For example, in case that a fluorogenic group of rhodamine type is used to prepare the latent fluorophore, the equivalent ratio of salicylic acid derivative to the fluorogenic group is 2:1.

In other words, the latent fluorophore according to the present invention may contain one salicylic acid moiety or two or more salicylic acid moieties.

The various latent fluorophores provided by the embodiments of the present invention can be used in various biochemical analyses. For example, a kit comprising a solution of SHL, a solution of any one of the latent fluorophores as stated above, and a solution of NADH or NADPH is provided. Thereafter, a specimen under test is mixed with the above solutions in an aerobic environment. At this time, if salicylic acid (a metabolite of aspirin) is present in the specimen under test, the fluorescence intensity will decrease. Therefore, the amount of salicylic acid present in the specimen under test can be determined by change in fluorescence intensity.

Furthermore, the various latent fluorophores provided by the embodiments of the present invention can be used in a biochemical analysis using a series of enzymes. For example, a kit comprising a solution of SHL, a solution of any one of the latent fluorophores as stated above, a solution of NAD(P)$^+$ and a solution of a NAD(P)$^+$-dependent dehydrogenase is provided. Thereafter, a specimen under test is mixed with the above solutions in an aerobic environment. At this time, if a substrate for the NAD(P)$^+$-dependent dehydrogenase is present in the specimen under test, the fluorescence intensity will increase. Therefore, the amount of salicylic acid present in the specimen under test can be determined by change in fluorescence intensity.

In addition, a kit comprising a solution of SHL, a solution of any one of the latent fluorophores as stated above, a solution of NAD(P)$^+$, a solution of a NAD(P)$^+$-dependent dehydrogenase, and a solution of a third enzyme which can catalyze formation of the substrate for the NAD(P)$^+$-dependent dehydrogenase in presence of a specific biochemical molecule, can be also provided. Thereafter, a specimen under test is mixed with the above solutions in an aerobic environment. At this time, if the specific biochemical molecule is present in the specimen under test, fluorescence intensity will increase. Therefore, the amount of the specific biochemical molecule present in the specimen under test can be determined by change in fluorescence intensity. In preferred embodiments, the NAD(P)$^+$-dependent dehydrogenase is selected from 3-hydroxybutyric acid dehydrogenase, cholesterol dehydrogenase, glucose dehydrogenase or glucose-6-phosphate dehydrogenase.

Based on the above, one embodiment of the present invention provides a method of fluorescence-based biochemical analysis for determination of the amount of salicylic acid in a specimen under test in a single-enzyme (i.e. SHL) system. Another embodiment of the present invention provides a method of fluorescence-based biochemical analysis for determination of the amount of a specific biochemical molecule in a two-enzyme (i.e. SHL and a NAD(P)$^+$-dependent dehydrogenase) system. Further another embodiment of the present invention provides a method of fluorescence-based biochemical analysis for determination of the amount of a specific biochemical molecule in a three-enzyme (i.e. SHL, a NAD(P)$^+$-dependent dehydrogenase and a third enzyme) system. In a preferred embodiment, the NAD(P)$^+$-dependent dehydrogenase is glucose-6-phosphate dehydrogenase and the third enzyme is hexose kinase.

In addition, other embodiments of the present invention provide a method of biochemical analysis using a series of enzymes (i.e. SHL, a NAD(P)$^+$-dependent dehydrogenase and one or more other enzymes). The NAD(P)$^+$-dependent dehydrogenase and other enzymes can be properly selected by a person having ordinary knowledge in this art according to the properties of the biochemical molecule to be analyzed without undue experiments.

EXAMPLES

Materials and Instruments $^1$H NMR and $^{13}$C NMR spectrums were obtained by Bruker AMX-500 spectrophotometer wherein chemical shift values were expressed in ppm relative to tetramethylsilane ($\delta$ unit); fluorescence intensity was measured by using a fluorescence-grade quartz cuvette and a spectrofluorometer, i.e. Horiba Jobin Yvon Fluoromax-4. The other chemicals are purchased from Acros, Aldrich, TCI or Sigma Chemical corporations and directly used without purification. As to the starting materials, salicylic acid derivatives and fluorogenic groups, were prepared according to the following theses: Cham, B. E.; John, D.; Bochner, F.; Imhoff, D. M.; Rowland, M. *Clin. Chem.* 1979, 25, 1420; d) Trinder, P. *Biochem. J.* 1954, 57, 301; and Wolfbeis, O. S.; Koller, E.; Hochmuth, P. *Bull. Chem. Soc. Jp.* 1985, 58, 731; the entire contents thereof are incorporated herein by reference. SHL is obtained from GDS Technology Inc. (USA). D-3-hydroxybutyric acid dehydrogenase is purchased from TOYOBO (Product Code: HBD-301). Cholesterol dehydrogenase is purchased from Genzyme Corp. All measurements were performed in 50 mM Tris-HCl (TRIZMA Base, Tris, pH8). The latent fluorophore is synthesized in DMSO and should be added to a Tris-HCl buffer before use to make the concentration of DMSO not exceed 0.1% (v/v).

Reaction Scheme

The main reaction flowchart according to one embodiment of the present invention is shown below:

Analysis of Fluorescence Profile of the Latent Fluorophores

Figure 1:
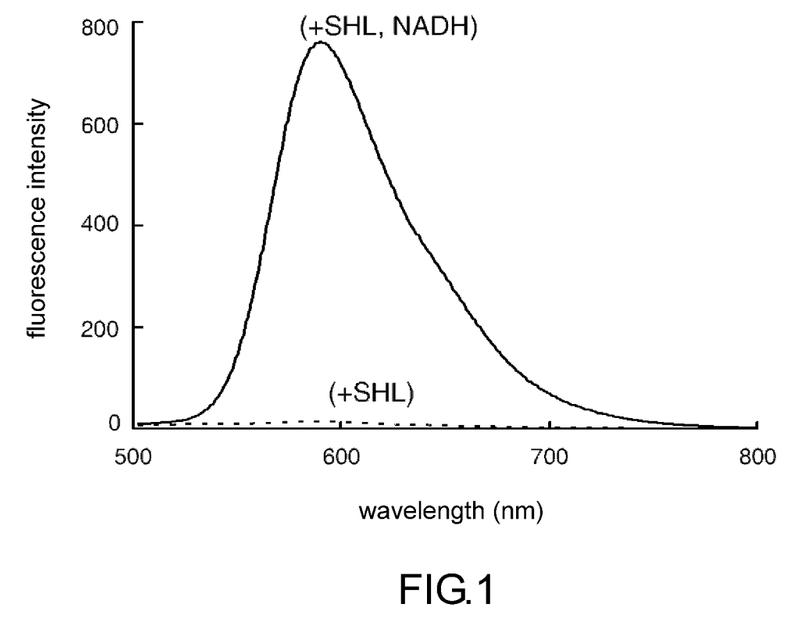
FIG. 1 shows the fluorescence-emitting property of the latent fluorophore according to one embodiment of the present invention.

The fluorescence profile of Compound C was analyzed in the presence of SHL and NADH in an aerobic environment. In case that Compound C (20 μM) was kept in a solution of SHL alone, in a solution of NADH alone, or in a Tris-HCl buffer solution (pH 8) even for several months, the fluorescence intensities of all were still near the baseline. However, in case that Compound C was kept in a solution containing both 1 unit of SHL and 1 mM NADH at 37□, the fluorescence intensity of Compound B increases 57 times in 90 minutes, as shown in FIG. 1 (dotted line representing the baseline). Furthermore, If 1 unit of SHL and 1 mM NADH were added to a Tris-HCl buffer solution containing Compound C, the fluorescence could be detected within several seconds; in the contrast, the fluorescence intensity would be still near the baseline even after 10 minutes if only SHL was added thereto.

Effect of Salicylic Acid on the Fluorescence Intensity

Figure 2:
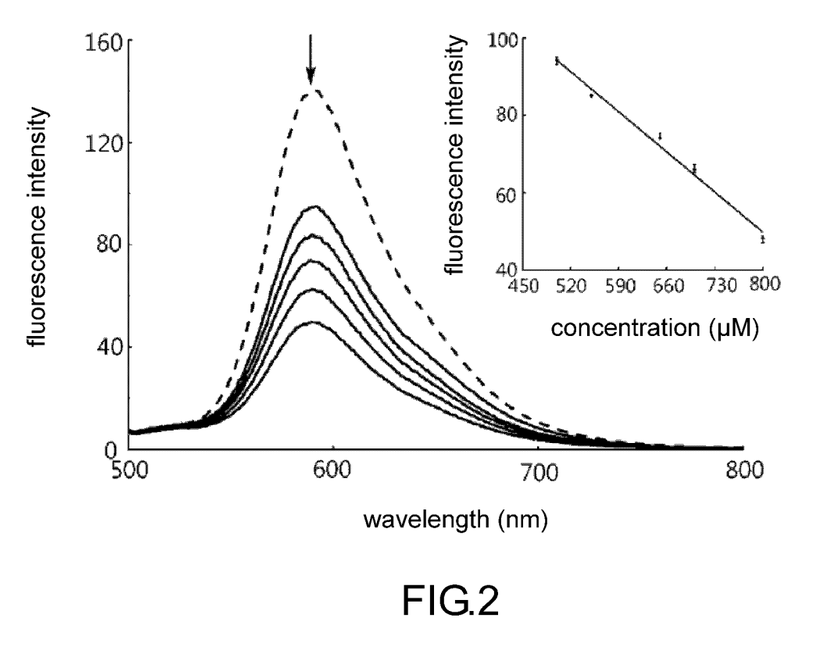
FIG. 2 shows the effect of salicylic acid on the fluorescence-emitting property of the latent fluorophore according to one embodiment of the present invention.

When salicylic acid was added to a solution containing SHL, Compound C and NADH under an aerobic condition, conversion of Compound C to a fluorogenic compound was inhibited; as a result, the fluorescence intensity of the solution decreased with the increase of the concentration of salicylic acid in the solution, as shown in FIG. 2 (the dotted line representing the fluorescence intensity before addition of salicylic acid). By plotting the fluorescence intensities vs. various concentrations of salicylic acid, it could be found that there existed a linear relationship between both in a concentration range of 200 to 700 μM. As salicylic acid is a metabolite of aspirin and it will exhibit toxicity at a blood level higher than 2.2 mM and may be fatal at a blood level above 4.3 mM, monitoring the blood level of salicylic acid is important in clinics. It can be known from this example that Compound C is useful in detection of the concentration of salicylic acid in a specimen.

Biochemical Analyses by Using a Latent Fluorophore in a Two-Enzyme System (I)

Figure 3:
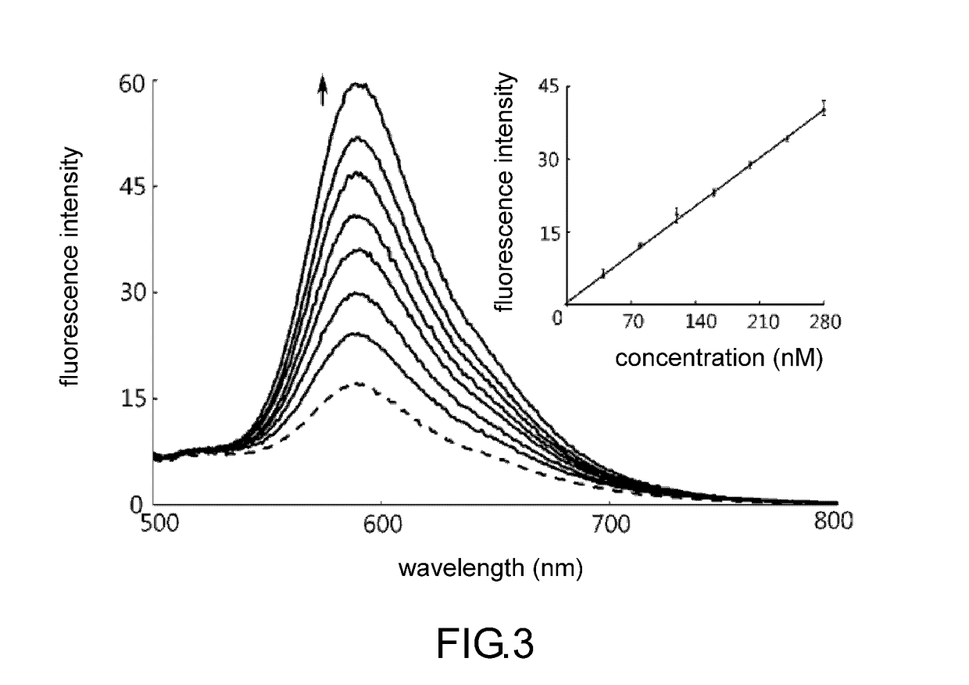
FIG. 3 shows the effect of 3-hydroxybutyric acid on the fluorescence-emitting property of the latent fluorophore according to one embodiment of the present invention.
Figure 4:
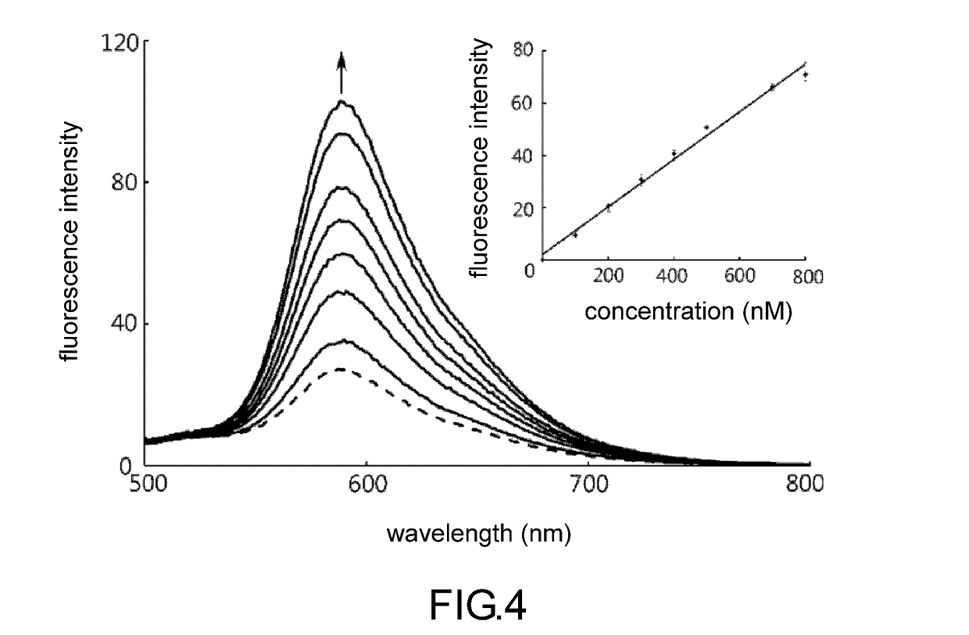
FIG. 4 shows the effect of cholesterol on the fluorescence-emitting property of the latent fluorophore according to one embodiment of the present invention.

Some biochemical analyses according to the present invention were performed in a two-enzyme system comprising SHL and either 3-hydroxybutyric acid dehydrogenase or chlolesterol dehydrogenase; wherein 3-hydroxybutyric acid dehydrogenase can oxidize 3-hydroxybutyric acid (involved in development of diabetes) and $NAD^+$ to form acetoacetate and NADH; and chlolesterol dehydrogenase can oxidize chlolesterol (involved in the development of cardiovascular diseases) with using NADH as electron acceptor. As shown in FIGS. 3 and 4, the fluorescence intensity of Compound C (10 μM) was near the baseline before addition of the substrate. After addition of the substrate, the fluorescence intensity significantly increased. By plotting the fluorescence intensities vs. the concentrations of the substrate, it could be found that there existed a linear relationship between both when the concentration of the substrate is in a range of 60 to 280 nM for 3-hydroxybutyric acid and in a range of 100 to 800 nM for chlolesterol. Accordingly, Compound C can be used to detect the amount of 3-hydroxybutyric acid or chlolesterol in a specimen if their concentrations are in an order of nanometer.

Biochemical Analyses by Using a Latent Fluorophore in a Two-Enzyme System (II)

Figure 5:
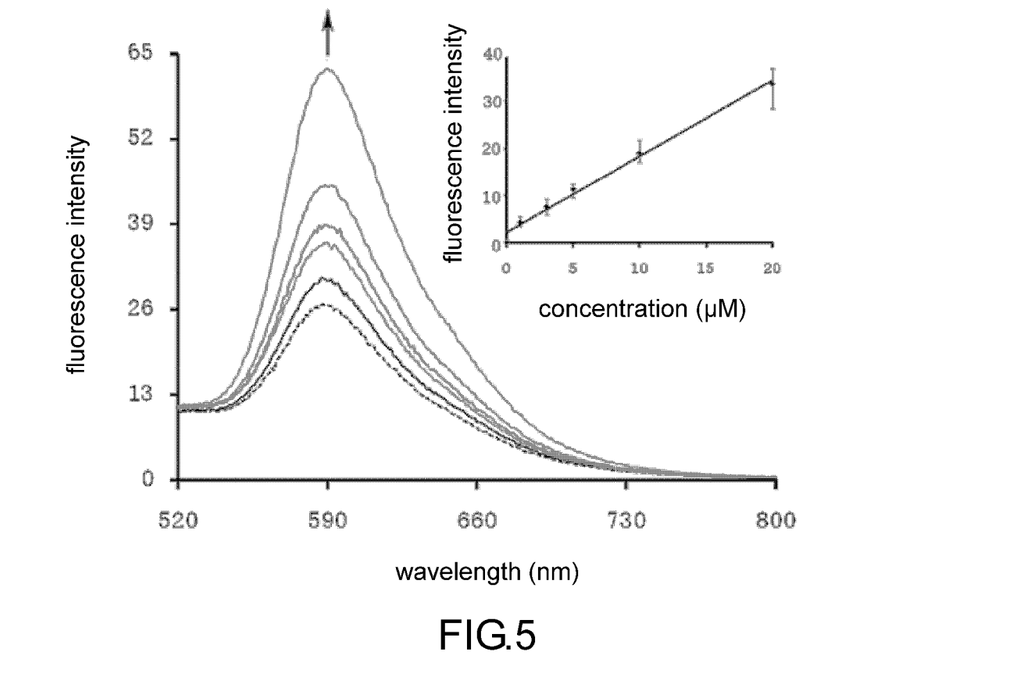
FIG. 5 shows the effect of glucose on the fluorescence-emitting property of the latent fluorophore according to one embodiment of the present invention.

Other biochemical analyses according to the present invention were performed in a two-enzyme system comprising SHL and glucose dehydrogenase. The result was shown in FIG. 5. It can be known from FIG. 5 that there exists a linear relationship between the fluorescence intensity of Compound C and the concentration of glucose when the concentration of glucose is in a certain range.

Biochemical Analyses by Using a Latent Fluorophore in a Three-Enzyme System

Figure 6:
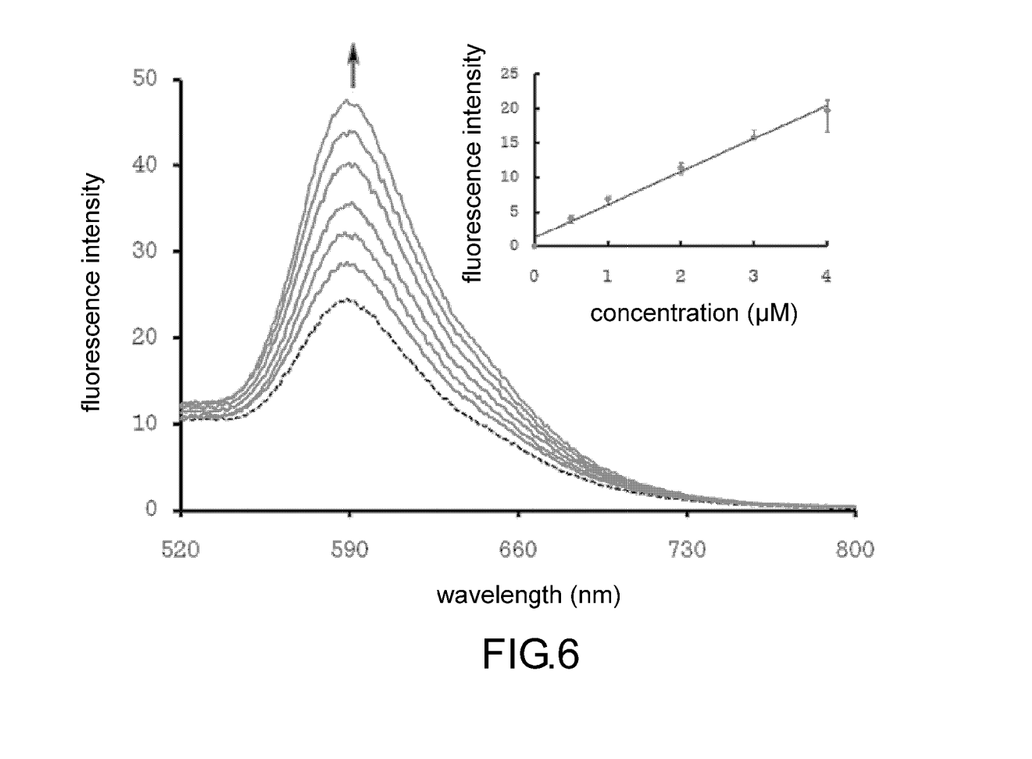
FIG. 6 shows the effect of ATP on the fluorescence-emitting property of the latent fluorophore according to one embodiment of the present invention.

Analysis of ATP was performed in a system comprising three enzymes: SHL, glucose-6-phosphate dehydrogenase and hexose kinase; $NAD^+$; glucose; and Compound C. The result was shown in FIG. 6. A series of reactions involved in this analysis are as follows:

Preparation of a Protected Latent Fluorophore

Compound A (0.43 mmole), Compound B (0.31 mmole), KI (0.042 mmole) and $K_2CO_3$ (0.37 mmole) were mixed with stirring in anhydrous DMF (2 mL) at room temperature under argon gas overnight. The resulting mixture was filtered after addition of water (50 mL), then extracted with $CH_2Cl_2$ (3×50 mL). The organic layer thus obtained was dried over $MgSO_4$, concentrated in vacuum, then purified by flash chromatography ($CH_2Cl_2$/toluene=¼), thereby obtaining the protected latent fluorophore as orange solid (yield: 42%, 70 mg). The analytical data thereof were as follows:

m.p. 187-190° C. $^1$HNMR (DMSO-$d_6$, 500 MHz) δ=1.71 (s, 6H); 5.42 (s, 2H); 7.22 (s, 1H); 7.32 (m, 3H); 7.56 (t, J=7.5 Hz, 1H); 7.62 (t, J=7.5 Hz, 1H); 7.91 (d, J=8.0 Hz, 1H); 7.96 (d, J=8.0 Hz, 1H); 8.13 (d, J=8.1 Hz, 1H); 8.21 (d, J=8.1 Hz, 1H). MS(EI) $C_{28}H_{18}N_2O_6S$ calc. 510.5 m/z=510.0. FT-IR: v/cm$^{-1}$=3075, 2941, 2868, 2371, 1742, 1724, 1615, 1587, 1536, 1502, 1440, 1378, 1288, 1268, 1191, 1144, 1042, 953, 902, 867, 842, 772, 693, 672 cm$^{-1}$ Deprotection of the Protected Latent Fluorophore The protected latent fluorophore (0.38 mmole) and trifluoroacetic acid (TFA)-$H_2O$ (1.75 mL, 9/1, v/v) were added to a 50 mL round-bottom flask provided with a magnetic stirrer and mixed with stirring for 12 hours. 50 mL of water was added to the resulting mixture and mixed for 30 minutes. The precipitate was filtered off and washed with cold water, thereby obtaining purified Compound C (yield: 0.08 mg, 0.17 mmol, 94%) as orange solid. The analytical data thereof were as follows:

m.p. 176-178° C. $^1$HNMR (DMSO-$d_6$, 500 MHz) δ=5.37 (s, 2H); 7.02 (d, J=8.1 Hz, 1H); 7.06 (s, 1H); 7.30 (d, J=8.1 Hz, 1H); 7.33 (s, 1H); 7.56 (t, J=7.5 Hz, 1H); 7.62 (t, J=7.5 Hz, 1H); 7.81 (d, J=8.1 Hz, 1H); 7.93 (d, J=8.1 Hz, 1H), 8.12 (d, J=8.0 Hz, 1H); 8.23 (d, J=8.1 Hz, 1H) MS (ESI) $C_{25}H_{14}N_2O_6S$ m/z=469 (M-1); MS (HESI): calc. 470.0573, m/z=469.470. FT-IR: v/cm$^{-1}$=3447, 2924, 2852, 2224, 1724, 1672, 1619, 1536, 1507, 1452, 1433, 1379, 1312, 1288, 1255, 1208, 1187, 1142, 1041, 1015, 948 cm$^{-1}$.

Analysis of the Concentration of a Biochemical Molecule to be Tested by Two Enzymes The measurement of fluorescence was performed at an excitation wavelength $\lambda_{ex}$ of 500 nm and an emission wavelength $\lambda_{em}$ of 595 nm. A Tris-HCl buffer containing Compound C(40 μM), SHL (0.2 unit), 3-hydroxy-butyric acid dehydrogenase (2 units) or cholesterol dehydrogenase (1 unit), NAD (10 μM), and 3-hydroxybutyric acid (0 to 0.5 μM) or cholesterol (0 to 0.5 μM) with a total volume of 1 mL was allowed to stand for 30 minutes at 25□. The measured fluorescence intensity after subtraction of baseline (concentration of the biochemical molecule to be tested is zero) intensity therefrom was plotted versus the concentration of the biochemical molecule to be tested.

Although the present invention has been described with reference to the foregoing preferred embodiments, it will be understood by the persons having ordinary knowledge in this art that these embodiments are merely used to illustrate the present invention but not intended to limit the present invention in any aspect. It should be noted that various equivalent modifications or replacements made on these embodiments are all embraced in the scope of the present invention. Accordingly, the protection scope of the present invention patent shall be subjected to the appended claims.

What is claimed is:

1. A salicylic acid derivative, having a structure as shown by any one of the following formulas:

formula II formula III

-continued formula IV wherein R₁ is selected from H or a $C_1$-$C_6$ alkyl, and the fluorogenic group is selected from a group consisting of wherein R₂ is selected from H or CN,
wherein R3 is selected from wherein each R4 is independently selected from a C1-C6 alkyl group, a benzyl group, CN or a halogen group.

2. The salicylic acid derivative according to claim 1, which can release a fluorogenic group under catalysis of salicyate hydroxylase (SHL).

3. The salicylic acid derivative according to claim 2, wherein the fluorescence emitted by the fluorogenic group has a wavelength above 500 nm.

4. The salicylic acid derivative according to claim 3, wherein the fluorescence emitted by the fluorogenic group has a peak emission wavelength of 550-650 nm.

5. A kit for biochemical analysis, comprising:
salicylate hydroxylase;
$NAD^+$ or $NADP^+$-dependent dehydrogenase;
$NAD^+$ or $NADP^+$; and
the salicylic acid derivative according to claim 1.

6. The kit for biochemical analysis according to claim 5, which further comprising a third enzyme for catalyzing formation of a substrate for the $NAD^+$ or $NADP^+$-dependent dehydrogenase.

7. A method of biochemical analysis, comprising:
providing a reagent comprising
salicylate hydrorxylase (SHL),
a salicylic acid derivative according to claim 1, and
NADH or NADPH;
adding a specimen under test to the reagent in an aerobic environment; and
measuring the fluorescence of the reagent, thereby determining the amount of salicylic acid present in the reagent.

8. A method of biochemical analysis, comprising:
providing a reagent comprising
salicylate hydrorxylase (SHL),
a salicylic acid derivative according to claim 1,
$NAD^+$ or $NADP^+$, and
a $NAD^+$ or $NADP^+$-dependent dehydrogenase;
adding a specimen under test to the reagent in an aerobic environment; and
measuring the fluorescence of the reagent, thereby determining the amount of a biochemical molecule present in the reagent.

9. The method according to claim 8, wherein the biochemical molecule is a substrate for the $NAD^+$ or $NADP^+$-dependent dehydrogenase.

10. The method according to claim 8, wherein the reagent further comprises a third enzyme for catalyzing formation of a substrate for the $NAD^+$ or $NADP^+$-dependent dehydrogenase in the presence of the biochemical molecule.

11. The method according to claim 10, wherein the third enzyme is hexose kinase.

12. The method according to claim 8, wherein the $NAD^+$ or $NADP^+$-dependent dehydrogenase is selected from 3-hydroxybutyric acid dehydrogenase, cholesterol dehydrogenase, glucose dehydrogenase or glucose-6-phosphate dehydrogenase.

* * * * *